| United States Patent [19] | [11] Patent Number: 4,667,050 |
| Woo et al. | [45] Date of Patent: May 19, 1987 |

[54] PREPARATION OF PYRETHROID PRECURSORS

[75] Inventors: Edmund P. Woo, Midland, Mich.; Joseph J. Laux, Cambridge, Mass.

[73] Assignee: The Dow Chemical Company, Midland, Mich.

[21] Appl. No.: 589,798

[22] Filed: Mar. 15, 1984

[51] Int. Cl.$^4$ .................. C07C 61/04; C07C 120/00; C07C 121/46

[52] U.S. Cl. ............................ 558/366; 204/157.69; 558/358; 558/378; 560/124; 560/174; 560/203

[58] Field of Search .......................... 260/464, 465.4; 560/124, 174, 203; 558/358, 366, 378

[56] References Cited

U.S. PATENT DOCUMENTS

| 3,997,586 | 12/1976 | Martel et al. | 560/124 X |
| 4,257,975 | 3/1981 | Punja | 260/465.4 |
| 4,362,670 | 12/1982 | Woo | 260/465 K |

OTHER PUBLICATIONS

Baker; Chemistry and Industry, 18, Oct. 1980, pp. 816–823.
Trost, et al.; J. Org. Chem., 40, (1975), pp. 3617–3619.
Trost, et al.; J. Org. Chem., 41, (1976), pp. 3215–3216.
Nakada, et al.; Bull. Chem. Soc. Japan., 52, (1979), pp. 1511–1514.
Bently, et al.; Pestic. Sci., 11, (1980), pp. 156–164.
Arlt, et al.; Angew. Chem. Int. Ed., 20, (1981), pp. 703–722.
Easton, et al.; J. Org. Chem., 27, (1962), pp. 3602–3605.

*Primary Examiner*—Joseph P. Brust

[57] ABSTRACT

Substituted vinylcyclopropane carboxylates, useful precursors to pyrethroid insecticides, are prepared by noble metal catalyzed addition of 1-methyl-3-buten-2-yl or 4-methyl-3-penten-1-yl carbonates or carboxylic acid esters to malonic acid diesters, alkyl acetates or alkyl cyanoacetates.

8 Claims, No Drawings

PREPARATION OF PYRETHROID PRECURSORS

BACKGROUND OF THE INVENTION

The present invention relates to a chemical process. More particularly, the present invention relates to a novel process for preparing allylic (2-propenyl) addition products of malonic acid (methane dicarboxylic acid) esters and nitriles that provides unique selectivity to the desired α-dimethyl malonic acid derivative.

In U.S. Pat. No. 4,257,957, there is provided a process for preparing pyrethroid starting reactants, especially 2(2,2-dichloroethenyl)-3,3-dimethylcyclopropane carboxylates. More particularly, such compounds were derived from (1,1-dimethyl-2-propenyl)malonates or (1,1-dimethyl-2-propenyl)malononitriles. Such starting reactants were in turn prepared by the palladium catalyzed hydrogenation of acetylenic compounds.

N. R. Easton et al., *J. Org. Chem.*, 27, 3602 (1962), disclosed the process for preparing such acetylenic compounds by alkylation of sodiomalonates with acetylenic halides and subsequently partially hydrogenating the resulting product. The process is not readily adapted to commercial practice due to a lack of ready availability of the starting reactants.

J. P. Genêt et al, *Tetrahedron Lett.*, 21, 3183–3185 (1980), reported the palladium catalyzed addition of a sterically hindered allylic radical to sodiomalonate esters and observed the unexpected regio- and stereoselectivity of the process to prepare primarily the product resulting from addition of the tertiary-substituted alkyl group. The authors concluded that this selectivity in product formation is due to steric hindrance at the neopentyl-substituted secondary center which directs the reaction towards the tertiary center.

In U.S. Pat. No. 4,362,670, one of the present inventors disclosed the general method of allyl group addition to carbon acids by the use of palladium catalyzed addition of allyl carbonates. The present invention in one embodiment constitutes a special adaption of this process in order to provide unique regio- and stereoselectivity in product distribution to provide addition at tertiary carbon centers of substituted allyl reactants.

A further embodiment of the present invention lies in the discovery that the reaction product of the present process may be employed without purification to remove isomeric by-products in a free radical initiated reaction with tetrahalomethane to prepare trihalomethyl-substituted malonic acid derivatives.

In a further embodiment of the present invention, there is provided a facile process for preparing 3(2,2-dichlorovinyl)-2,2-dimethyl-1-cyclopropane carboxylic acid and esters thereof in relatively high yields starting from freely available starting reactants.

SUMMARY OF THE INVENTION

According to the present invention, there is provided a process for preparing additional products of 3-methylbutenyl alkylating agents wherein at least about 50 percent on a molar basis of such addition products correspond to the formula:

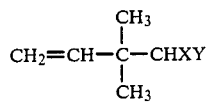  (I)

wherein X is —C(O)R', —CN or hydrogen, and Y is —C(O)OR$_1$, wherein R' is R$_1$ or OR$_1$, and R$_1$ is C$_{1-4}$ alkyl; comprising contacting an allylic carbonate or an allylic ester of a carboxylic acid corresponding to the formula:

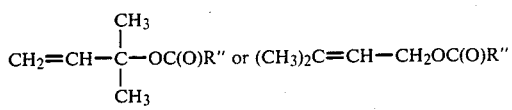

wherein R" is R$_2$ or OR$_2$ and R$_2$ is C$_{1-20}$ alkyl; with a dialkyl malonate, alkyl acetate, alkyl cyanoacetate or alkali metal derivative thereof corresponding to the formula:

ZCHXY wherein Z is hydrogen or an alkali metal and X and Y are as previously defined, in the presence of a noble metal catalyst under alkylation conditions.

The above prepared addition products are valuable intermediates for preparation of pyrethroid insecticides. A unique advantage of their use in, e.g., a process as described in U.S. Pat. No. 4,257,975, is that isomeric by-products do not participate or interfere with addition of a tetrahalomethyl group under free radical reaction conditions. Accordingly, the mixture of products and isomeric by-products prepared by the present invention need not be distilled or otherwise purified to separate only 1,1-dimethyl-2-propenyl derivatives of formula I for further reaction. Instead, a relatively facile separation may be performed in order to purify the product obtained from the free radical addition reaction.

Accordingly, the present invention additionally comprises a process for preparing free radical induced addition products of tetrahalomethane, trifluoromethyltrihalomethane or di(trifluoromethyl)dihalomethane compounds and compounds of formula I comprising the steps of:

(a) preparing a mixture of addition products of 3-methyl-1-butenyl alkylating agents wherein at least 50 percent on a molar basis of such addition products correspond to the formula:

  (I)

wherein X is —C(O)R', —CN or hydrogen, and Y is —C(O)OR$_1$, and R' is R$_1$ or OR$_1$, and R$_1$ is C$_{1-4}$ alkyl; comprising contacting an allylic carbonate or an allylic ester of a carboxylic acid corresponding to the formula:

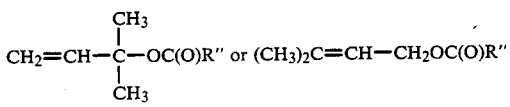

wherein R" is R$_2$ or OR$_2$ and R$_2$ is C$_{1-20}$ alkyl; with a dialkyl malonate, alkyl acetate, alkyl cyanoacetate or alkali metal salt thereof corresponding to the formula:

ZCHXY wherein Z is hydrogen or an alkali metal and X and Y are as previously defined, in the presence of a noble metal catalyst under alkylation conditions;

(b) contacting the above prepared mixture of addition products with a tetrahalomethane, trifluoromethyltrihalomethane, or di(trifluoromethyl)dihalomethane according to the formula:

CABDE wherein A and B are halogen or —$CF_3$, and D and E are halogens under free radical addition conditions to prepare a trihalomethyl-, trifluoromethyldihalomethyl- or di(trifluoromethyl)halomethyl-substituted addition product; and (c) separating the trihalomethyl-, trifluoromethyldihalomethyl- or di(trifluoromethyl)halomethyl-substituted addition product.

While any free radical induced addition process may suitably be employed to prepare the trihalomethyl-substituted addition products above-described, a particularly preferred method has now been discovered that in one step causes both free radical addition and ring closure to form the cyclopropane moiety in one convenient step. Prior art processes as exemplified in U.S. Pat. No. 4,257,975 first prepared the 2-methyl-3,5,5-trihalo-2-pentyl malonic acid derivative and thereafter cyclized by addition of base.

Accordingly, it is a further embodiment of the present invented process to prepare substituted 2,2-dimethyl-1-cyclopropane carboxylic acid derivatives corresponding to the formula:

$$ABC=CH-CH\underset{\underset{CH_3}{\diagup}\underset{CH_3}{\diagdown}}{\overset{\diagdown\;\;\diagup}{\underset{C}{\rule{0pt}{0pt}}}}CH-COOH \quad (II)$$

wherein A is halogen or —$CF_3$, and B is halogen, comprising the steps of:

(a) preparing a mixture of addition products of 3-methyl-1-butenyl alkylating agents wherein at least 50 percent on a molar basis of such addition products correspond to the formula:

$$CH_2=CH-\underset{\underset{CH_3}{|}}{\overset{\overset{CH_3}{|}}{C}}-CHXY \quad (I)$$

wherein X is —C(O)R', —CN or hydrogen, and Y is —C(O)$OR_1$, wherein R' is $R_1$ or $OR_1$, and $R_1$ is $C_{1-4}$ alkyl; comprising contacting an allylic carbonate or an allylic ester of a carboxylic acid corresponding to the formula:

$$CH_2=CH-\underset{\underset{CH_3}{|}}{\overset{\overset{CH_3}{|}}{C}}-OC(O)R'' \text{ or } (CH_3)_2C=CH-CH_2OC(O)R''$$

wherein R'' is $R_2$ or $OR_2$ and $R_2$ is $C_{1-20}$ alkyl; with a dialyl malonate, alkyl acetate, alkyl cyanoacetate or alkali metal salt thereof corresponding to the formula:

ZCHXY wherein Z is hydrogen or an alkali metal and X and Y are as previously defined, in the presence of a noble metal catalyst under alkylation conditions;

(b) contacting the above prepared mixture of addition products with a tetrahalomethane, trifluoromethyltrihalomethane, or di(trifluoromethyl)dihalomethane corresponding to the formula:

CABDE wherein A and B are halogen or —$CF_3$, and D and E are halogens, in the presence of a free radical initiating amount of a copper salt and a primary amine under free radical addition reaction conditions to prepare a trihalomethyl-, trifluoromethyldihalo- or di(trifluoromethyl)halo-substituted addition product corresponding to the formula:

$$ABDC-CH_2-CH\underset{\underset{CH_3}{\diagup}\underset{CH_3}{\diagdown}}{\overset{\diagdown\;\;\diagup}{\underset{C}{\rule{0pt}{0pt}}}}CXY \quad (III)$$

wherein A, B, D, X and Y are as previously defined;

(c) separating the trihalomethyl-, trifluoromethyldihalo- or di(trifluoromethyl)halo-substituted addition product according to formula III;

(d) contacting the trihalomethyl-, trifluoromethyldihalo- or di(trifluoromethyl)halo-substituted addition product according to formula III with an alkali metal hydroxide to prepare a saponified elimination product corresponding to the formula:

$$ABC=CH-CH\underset{\underset{CH_3}{\diagup}\underset{CH_3}{\diagdown}}{\overset{\diagdown\;\;\diagup}{\underset{C}{\rule{0pt}{0pt}}}}C-(COOM)_2$$

wherein M is an alkali metal, and A and B are as previously defined; and (e) neutralizing and decarboxylizing the product of step (d) to prepare the substituted 2,2-dimethyl-1-cyclopropane carboxylic acid corresponding to formula (II).

DETAILED DESCRIPTION OF THE INVENTION

The previously described allylic carbonates and allylic esters of lower carboxylic acids (3-methylbutenyl alkylating agents) appear to be uniquely adapted to preparation of the desired allylated reaction products. It has been discovered that the desired regio- and stereoselectivity to products comprising at least about 50 percent on a molar basis of the 1,1-dimethyl-2-propenyl derivatives is obtained only by operation according to the present reaction parameters. For example, N. Ono et al., *J. Chem. Soc. Chem. Commun.*, 821 (1982) found that reaction of 3-nitro-3-methylbutene fails to provide similar selectivity. Reported yields of the desired dimethyl (1,1-dimethylallyl)malonate upon reaction of the above compound with sodiodimethyl malonate were 27 percent compared to 73 percent for the undesired isomer.

Similarly, the reaction of geranyl acetate, $(CH_3)_2C=CHCH_2CH_2C(CH_3)=CHCH_2OAc$, with sodiodiethyl malonate has been reported to provide 90–95 percent selectivity to the isomer resulting from attack at the primary carbon terminus. B. M. Trost et al., *J. Org. Chem.*, 41, 3215 (1976).

The present inventors have obtained like results by employing allylic reagents other than those herein specified and required by the claims.

Preferred allylic reactants are acetates due to their availability. A particularly preferred allylic reactant is 2-methyl-3-buten-2-yl acetate. However, a desirable feature of the use of allylic carbonates is that the alkylation need not be performed in the presence of base, or by generation of the sodium derivative of the dialkyl malonate, alkyl carboxyacetates or cyanoacetate in as much as the allylic carbonate is sufficiently reactive of its own accord. The teachings of U.S. Pat. No. 4,362,670 as to the use of allylic carbonate reactants are hereby incorporated by reference.

The malonate, alkyl acetate, alkyl cyanoacetate or alkali metal salts thereof (interchangeably referred to hereafter as carbon acids) are well-known compounds or compounds readily prepared by known techniques. Malonic acid esters, acetoacetate esters and sodium salts thereof are preferably employed for the reaction, particularly with allylic acetates. Especially preferred carbon acids are dimethyl malonate, methyl acetoacetate and sodium derivatives thereof. Sodium derivatives of carbon acids may be conveniently prepared by reaction of sodium hydride and the corresponding malonate, alkyl carboxyacetate or cyanoacetate.

The process is conducted in the presence of a noble metal catalyst. Suitable noble metals include palladium, platinum, osmium, ruthenium, iridium, rhodium, nickel and cobalt catalysts either in a homogeneous or a heterogeneous state. Preferred are palladium catalysts further identified in U.S. Pat. No. 4,362,670 which teaching has been previously incorporated herein by reference. Especially preferred noble metal catalysts are homogeneous palladium complexes, especially tetrakis(-triphenylphosphine)palladium (0) or triphenylphosphine-bis(dibenzalacetone)palladium (0).

The process may be performed in an inert solvent if desired. An example of such a suitable solvent is tetrahydrofuran. Additional suitable solvents include ethers such as alkyl ethers and polyoxyalkylene ethers, aromatic compounds, ketones, esters, alkyl carbonates, alkylene carbonates and chlorinated hydrocarbons. Desirably, the process is conducted under an inert atmosphere.

The palladium catalyst is employed in a catalytically effective amount. Generally, minor amounts from about 0.1 to about 10 percent by weight palladium based on the amount of allylic reagent and preferably from about 0.1 to about 2 percent are employed.

The reaction is allowed to proceed to substantial completion. Generally, reaction times of several minutes to several hours are sufficient. Upon completion of the reaction, the solvent, if used, may be removed by distillation. The reaction may be quenched with water and the desired addition products extracted. Suitably, ether may be employed as the extractant. Alternate means of recovering the desired addition products may, of course, also be employed. Removal of the extraction solvent produces the desired mixture of addition products in substantial yield.

The isomeric addition products obtained in the present process are further identified for purposes of clarity in the following manner:

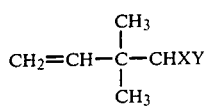

and

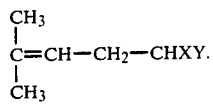

The reaction parameters, including the identity of the initial reactants, determine the particular ratio of isomeric products obtained. Typical results provide a yield of tertiary addition product (isomer 1) of at least about 50 percent as previously described. Preferably, the desired isomer is obtained in a molar ratio of at least 2:1, e.g., at least about 67 percent of Isomer I, and most preferably at least 3:1, e.g., at least about 75 percent of Isomer I, compared to the product obtained by addition at the primary center (isomer 2).

As previously explained, this regio- and stereoselectivity of the present process to preferentially prepare isomer 1 is believed to be unique to the present limited reaction conditions and totally unexpected based on the knowledge available from the prior art.

As has been previously explained, the isomeric mixture prepared by the allylic addition may be subsequently employed in a free radical addition according to techniques known in the art and taught, for example, in U.S. Pat. No. 4,257,975, which teachings were previously incorporated herein by reference.

However, the free radical addition reaction preferred by the present inventors is to employ a copper catalyst especially a homogeneous copper (I) salt such as CuCl, $CuNO_3$, $Cu_2CO_3$, $Cu_2SO_4$, CuBr, CuI, or CuOAc, in combination with a primary amine. Suitable primary amines include tertiary butylamine, cyclohexylamine, ethanolamine, isopropylamine, n-octylamine, etc. A preferred primary amine is tertiary butylamine. Advantageously, the primary amine component of the redox system serves as a base to cause addition and ring closure in one convenient process. Moreover, practice according to the present invention instead of by use of a strong base for the ring closure, provides greater selectivity to the desired cyclopropane derivative and eliminates by-product chloroacetylene derivative formation.

When the free radical addition is performed in the preferred manner employing a copper (I) salt and a primary amine, the resulting product is the cyclopropane derivative corresponding to the formula:

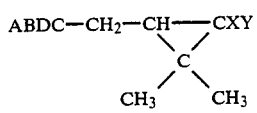

wherein A, B, D, X and Y are as previously defined.

Alternative free radical addition processes include the use of a peroxide, light, or the use of the noble metal catalyst employed in the allyl addition step. Yields, however, tend to be reduced where alternate processes are employed, and the product is not the ring closed reaction product.

The free radical addition is performed in known manner employing the mixture of isomers obtained from the allyl addition reaction. Even the presence of small amounts of unreacted carbon acid has not been found to be detrimental to the reaction. The addition may be performed in an inert solvent which may be an excess of the tetrahalomethane, trifluoromethyltrihalomethane or di(trifluoromethyl)dihalomethane employed in the process. The reaction is suitably conducted at elevated temperatures. Preferred addition reactants are carbon tetrachloride or bromotrichloromethane.

Separation of the product mixture may be performed by any standard technique. Distillation is the preferred method of separation.

The remaining process step requires the elimination of hydrogen halide to regenerate the desired vinyl functionality. Because the final product is desirably a monocarboxylic acid derivative, the base induced elimination may advantageously be combined with a saponification so that upon heating, decarboxylation of one carboxyl group may be simultaneously effected. Accordingly, the saturated cyclopropane derivative is heated in the presence of a base until elimination of hydrogen chloride to prepare the vinyl moiety is substantially complete.

Preferred bases include the alkali metal hydroxides which have advantageously been found to additionally cause saponification of the cyano or alkoxycarbonyl functionality. Especially preferred is sodium hydroxide.

The elimination and saponification process is conducted in a suitable medium such as aqueous alcoholic solutions, especially aqueous ethanol or methanol solutions. A particularly preferred aqueous alcoholic system is a mixture of water and methanol. Suitably, the alcohol comprises from about 5 percent to about 75 percent of the solution. The process is conducted at elevated temperatures. Suitable are temperatures from about 50° C. to about 130° C., preferably from about 80° C. to about 100° C. Elevated pressures may be employed if desired.

Neutralization of the saponified reaction product is readily accomplished by acidification of the reaction medium with any suitable acid. Normally, merely neutralizing the caustic with an equivalent amount of a strong acid is sufficient. Decarboxylation occurs in known manner upon heating of the diacid.

The resulting 3(vinyl)-2,2-dimethyl-1-cyclopropane carboxylic acid product is recovered by standard techniques, e.g., extraction, and employed as is for the preparation of pyrethroid products according to known methods such as esterification with the appropriate phenolic derivative.

SPECIFIC EMBODIMENTS

Having described the invention, the following examples are provided as further illustrative and are not to be construed as limiting.

EXAMPLE 1

Preparation of 2-Methyl-3-buten-2-yl Acetate (Reactant)

To a stirred solution of 2-methyl-3-buten-2-ol (86.13 g, 1.0 mole), triethylamine (101.19 g, 1.3 mole), and 4-dimethylaminopropyridine (25.0 g, 0.2 mole) at 0° C. is added dropwise acetic anhydride (102.09 g, 1.15 mole) in $CH_2Cl_2$ (700 ml). The mixture is stirred at 0° C. for 5 hours and at room temperature overnight. Water is then added and the $CH_2CL_2$ layer separated. The aqueous layer is extracted with $CH_2Cl_2$ (3×300 ml) and the combined $CH_2Cl_2$ solution is washed with cold 1N HCl (300 ml), water (330 ml) and dried over anhydrous $MgSO_4$. Distillation of the $CH_2Cl_2$ solution gives 2-methyl-3-buten-2-yl acetate (113.07 g), 88 percent, boiling point 59° C. (80 mm Hg).

EXAMPLE 2

Preparatiom of Methyl 2-Methyl-3-buten-2-yl Carbonate (Reactant)

To a solution of 2-methyl-3-buten-2-yl (8.61 g, 100 mmoles) in 10 ml tetrahydrofuran at −78° C. is added a solution of n-butyl lithium in hexane (63 ml, 1.6M). After 10 minutes of stirring, methyl chloroformate (15 ml) is added dropwise and the resulting mixture allowed to warm to room temperature. Distillation of the residue after solvent removal gives methyl 2-methyl-3-buten-2-yl carbonate (13.50 g), 95 percent, boiling point 90° C. (150 mm Hg).

EXAMPLE 3

Alkylation of Dimethyl Malonate

A mixture of bis(dibenzalacetone)palladium (0) (0.23 g, 0.4 mmole) and triphenylphosphine (0.84 g, 3.2 mmoles) in tetrahydrofuran (10 ml) is stirred at room temperature under argon for a few minutes to generate the catalytically active species. To the catalyst solution is added 2-methyl-3-buten-2-yl acetate (51.27 g, 400 moles) prepared according to Example 1 and a tetrahydrofuran solution of preformed dimethyl sodiomalonate prepared from sodium hydride (10.77 g) and dimethyl malonate (59.45 g, 450 mmoles). The resulting solution is maintained at reflux overnight under argon. The solvent (tetrahydrofuran) is removed by distillation and the residue after quenching with water is extracted with ether. After drying the ether is evaporated to leave 90 g of residue. Distillation at reduced pressure gives 69.0 g (86.1 percent) of colorless liquid (boiling point 110° C., 3.5 mm) shown by gas-liquid chromatography, infrared and nuclear magnetic resonance to be a 3:1 mixture of dimethyl(1,1-dimethylallyl)malonate and dimethyl(3,3-dimethylallyl)malonate.

EXAMPLE 4

The reaction conditions of Example 3 are substantially repeated excepting that methyl 2-methyl-3-buten-2-yl carbonate prepared according to the procedure of Example 2 is used as the alkylating agent and dimethyl malonate instead of its sodium salt is used as the carbon acid. The product comprises the same isomers in essentially the same ratio as in Example 3.

EXAMPLE 5

Addition of Carbon Tetrachloride

A portion of the reaction mixture prepared according to Example 3 (3.0 g, 15 mmoles of malonic ester) cuprous chloride (0.044 g), t-butylamine (5 ml) and carbon tetrachloride (4.6 g) is refluxed for 30 hours. The excess amine and carbon tetrachloride are removed on a rotary evaporator and the residue diluted with water and extracted with ether. After drying and removal of ether, the residue is subjected to bulb-to-bulb distillation at 0.05 mm Hg, 100° C. The desired compound, 1,1-dimethoxycarbonyl-2,2-dimethyl-3-(2,2,2-trichloroethyl)cyclopropane is obtained as a semi-solid (3.10 g), 90 percent yield. The structure is confirmed by mass spectrometry, infrared and nuclear magnetic resonance spectroscopy.

EXAMPLE 6

Addition of Bromotrichloromethane

A portion of the product mixture prepared according to Example 3 (30.04 g, 150 mmoles of malonic ester) is heated at 90° C. for 1 hour with bromotrichloromethane (119 g, 600 mmoles) and benzoyl peroxide (0.73 g). Distillation of low boilers gives 47 g of residue shown to be 93 percent pure by gas-liquid chromatography. The infrared and nuclear magnetic resonance spectra of the product are consistent with the structure of methyl 2-methoxycarbonyl-3,3-dimethyl-4-bromo-6,6,6-trichlorohexanoate. The addition production of dimethyl-(3,3-dimethylallyl)malonate is apparently unstable under the distillation conditions.

EXAMPLE 7

Addition of Carbon Tetrachloride

The reaction conditions of Example 6 are substantially repeated employing carbon tetrachloride. A 90 percent yield of methyl 2-methoxycarbonyl-3,3-dimethyl-4,6,6,6-tetrachlorohexanoate is obtained after about 16 hours of heating at 90° C.

EXAMPLE 8

Preparation of 3-(2,2-Dichlorovinyl)-2,2-dimethyl-1-cyclopropanecarboxylic Acid A mixture of 1,1-dimethoxycarbonyl-2,2-di-methyl-3-(2,2,2-trichloroethyl)cyclopropane (8.7 g, 27.3 mmoles) prepared according to the procedure of Example 5, methanol (8 ml) and 20 percent aqueous NaOH (35 ml, 175 mmoles) is heated at 100° C. for 5 hours. Acidification of the solution with concentrated HCl precipitates 2(2,2-dichlorovinyl)-3,3-dimethylcyclopropane dicarboxylic acid (6.44 g, 93 percent) which is subjected to bulb-to-bulb distillation at 0.3 mm Hg, 110° C.–150° C. The monoacid, 2(2,2-dichlorovinyl)-3,3-dimethylcyclopropane carboxylic acid (5.31 g), distills as it is formed from decarboxylation in about 100 percent yield. The structure of the monoacid is confirmed by its infrared and nuclear magnetic resonance spectra.

EXAMPLE 9

Alkylation with Methyl Acetoacetate

A mixture of bis(dibenzalacetone)palladium (0) (0.0575 g), tricyclohexylphosphine (0.1122 g) and 2-methyl-3-buten-2-yl acetate (1.28 g, 10 mmoles) prepared according to the process of Example 1 is stirred under argon for 10 minutes. To this solution is added a solution of the sodium salt of methyl acetoacetate (1.16 g, 10 mmoles of neutral acetate) in tetrahydrofuran (10 ml). After a period of 5 hours at reflux, the mixture is diluted with water and extracted with ether. The ether solution upon distillation gives 1.16 g of clear liquid whose composition is shown by gas chromatography to be 21 percent unreacted methyl acetoacetate and 79 percent of two products in the ratio of 96:4. These products were separated by preparative gas chromatography and were identified by infrared and nuclear magnetic resonance spectroscopic techniques as methyl 2-acetyl-3,3-dimethyl-4-pentenoate and methyl 2-acetyl-5-methyl-4-hexenoate, respectively.

EXAMPLE 10

Alkylation of Dimethyl Malonate with Methyl 3-Methyl-2-buten-1-yl Carbonate The reaction conditions of Example 4 are substantially repeated excepting that an equimolar mixture of dimethyl malonate and methyl 3-methyl-2-buten-1-yl carbonate is reacted in the presence of 1 mole percent of tetrakis(triphenylphosphine)palladium (0). The product is a mixture of 72 percent dimethyl (1,1-dimethylallyl)-malonate and dimethyl(3,3-dimethylallyl)malonate.

What is claimed is:

1. A process for preparing a substituted cyclopropane compound corresponding to the formula:

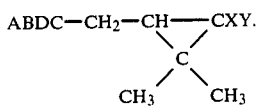

wherein A and B independently are trifluoromethyl or halo, D is halo, X is —C(O)R', —CN or hydrogen, and Y is —C(O)OR$_1$ wherein R' is R$_1$ or —OR$_1$ and R$_1$ is C$_{1-4}$ alkyl; comprising the steps of:

(a) contacting a 3-methylbutenyl alkylating agent corresponding to the formula:

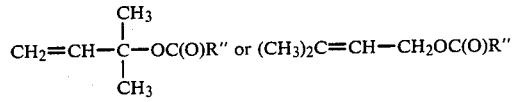

wherein R'' is R$_2$ or OR$_2$ and R$_2$ is C$_{1-20}$ alkyl; with a carbon acid or alkali metal derivative thereof corresponding to the formula:

wherein Z is hydrogen or an alkali metal and X and Y are as previously defined, in the presence of a noble metal catalyst under alkylation conditions such that at least about 50 percent on a molar basis of such addition products corresponds to the formula:

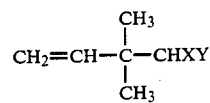

wherein X and Y are as previously defined;

(b) contacting the mixture of addition products prepared in step (a) with a tetrahalomethane, trifluoromethyltrihalomethane, or di(trifluoromethyl)dihalomethane corresponding to the formula:

wherein A, B and D are as previously defined and E is halogen, in the presence of a copper (I) salt and a primary amine under free radical addition reaction conditions.

2. A process according to claim 1 wherein the 3-methylbutenyl alkylating agent is 2-methyl-3-buten-2-yl acetate, 3-methyl-2-buten-1-yl acetate, methyl 2-methyl-3-buten-2-yl carbonate or methyl 3-methyl-2-buten-1-yl carbonate.

3. A process according to claim 1 wherein the carbon acid is dimethyl malonate, methyl acetoacetate, methyl cyanoacetate or an alkali metal derivative thereof.

4. A process according to claim 1 wherein the noble metal catalyst is a homogeneous palladium catalyst.

5. A process according to claim 1 wherein the homogeneous palladium catalyst is tetrakis(triphenylphosphine)palladium (0) or triphenylphosphine-bis(dibenzalacetate)palladium (0).

6. A process according to claim 1 wherein the copper (I) salt is $CuCl$, $CuNO_3$, $Cu_2CO_3$, $Cu_2SO_4$, $CuBr$, $CuI$ or $CuAc$.

7. A process according to claim 1 wherein the primary amine is tertitary butylamine.

8. A process according to claim 1 wherein the mixture of addition products from step (a) is contacted with carbon tetrachloride or bromotrichloromethane.

* * * * *